United States Patent [19]
Ford et al.

[11] Patent Number: 5,516,977
[45] Date of Patent: May 14, 1996

[54] XENOGENEIC TISSUE IMPLANT IN EAR PINNA

[75] Inventors: Brian Ford, Sunnyvale; Hideto Kaneshima, Palo Alto, both of Calif.

[73] Assignee: Systemix, Inc., Palo Alto, Calif.

[21] Appl. No.: 169,323

[22] Filed: Dec. 17, 1993

[51] Int. Cl.$^6$ .......................... A01K 67/00; A61K 49/00
[52] U.S. Cl. ............... 800/2; 800/DIG. 3; 800/DIG. 4; 800/DIG. 5; 435/240.2; 424/93.7; 424/578
[58] Field of Search ................................. 800/2, DIG. 3, 800/4, 50; 435/240.2; 424/9

[56] References Cited

FOREIGN PATENT DOCUMENTS 9116910  11/1991  WIPO.

OTHER PUBLICATIONS

R Namikawa et al (1988) Science 242:1684–1686.
Santos et al., "Anti–CD4 Abrogates Rejection and Reestablishes Long Term Tolerance to Syngeneic Newborn Hearts Grafted in Mice Chronically Infected with Trypanosoma Cruzi," J. Exp. Med. (1992) 175: 29–39.
Mukamel et al., "A Mouse Ear Reaction for Assessment of Human Lymphocyte Immunocompetence," Immunobiol. (1985) 169: 21–29.
Meyvisch & Mareel, "Site Induced Differences in Spontaneous Metastasis of MO4 Mouse Fibrosarcoma Cells," Invasion Metastasis. (1985) 5: 185–192.
Fulmer et al., "Transplantation of Cardiac Tissue into the Mouse Ear," American Journal of Anatomy (1963) 113: 273–281.
Namikawa et al., "Long Term Human Hematopoiesis in the SCID–hu Mouse," J. Exp. Med. (1990) 172: 1055–1063.
McCune, "HIV–1: The Infective Process In Vivo" Cell (1991) 64: 351–363.
Mombaerts et al., "RAG–1–Deficient Mice Have no Mature B and T Lymphocytes" Cell (1992) 68: 869–877.
McCune et al., "The SCID–hu Mouse: Murine Model for the Analysis of Human Hematolymphoid Differentiation and Function," Science (1988) 241: 1632–1639.

Primary Examiner—Jacqueline M. Stone
Assistant Examiner—Bruce R. Campell
Attorney, Agent, or Firm—Bertram I. Rowland; Pamela J. Sherwood

[57] ABSTRACT

Immunocompromised hosts comprising xenogeneic fetal lymph node tissue implanted in the ear pinna are provided. The chimeric hosts are prepared by inserting the xenogeneic lymph node tissue into the ear pinna and closing the incision. The tissue is found to be rapidly vascularized and can be productively infected with HIV.

10 Claims, No Drawings

XENOGENEIC TISSUE IMPLANT IN EAR PINNA

INTRODUCTION

1. Technical Field

The field of this invention is immunocompromised mammals comprising xenogeneic tissue.

2. Background

The use of heterologous transplants in a host has found wide application in research and therapy. The ability to transplant tissue from one host to another allows for opportunities of scientific investigation which are not available in the source host. Of particular interest has been the transfer of xenogeneic tissue into an immunocompromised host for study of the tissue, its response to drugs and changes in the environment of the tissue. The foreign tissue may be capable of functioning and growing. In this way, various aspects of the foreign tissue may be studied in an environment simulating the natural environment.

The report of transplantation of normal human fetal tissue into a scid/scid mouse has been reported. (McCune, et al. (1988) Science 241:1632–1639) The authors describe the introduction of human thymus and lymph node tissue into the kidney capsule of a scid/scid mouse. The fetal tissue was found to grow and function, and the thymus assumes a substantially normal architecture, where the organs were capable of interacting.

The kidney capsule as a site for introduction of xenogeneic tissue is good in general, however it has limitations for some tissues, such as lymph nodes. There is, therefore, interest in being able to develop alternative sites and methods for introduction of xenogeneic tissue into anatomical sites of target hosts.

RELEVANT LITERATURE

A description of the SCID-hu mouse may be found in McCune, J. M., et al., Science (1988), 241:1632–1639, Namikawa, R., et al., J. Exp. Med., (1990), 172:1055–1063 and McCune, et at., Ann. Rev. Immunol. (1991), 9:395–429.

Injection of human tumor cells into the ears of immune suppressed NZW mice is described in Mukamel, et al. (1985) Immunobiology 169:21–29. Meyvisch & Mareel (1985) Invasion Metastasis 5:185–192 disclose the implantation of mouse fibrosarcoma cells in the ear pinna.

The mouse ear has also been used as a site for implantation of syngeneic heart tissue, described in dos Santos, et al. (1992) J. Experimental Medicine 175:29–39 and Fulmer, et al. (1963) American Journal of Anatomy 113:273.

SUMMARY OF THE INVENTION

Immunocompromised hosts are provided, comprising xenogeneic functioning hematolymphoid tissue implanted in the ear pinna. The method of preparation involves inserting the xenogeneic tissue into the ear pinna and closing the incision. The tissue is rapidly vascularized and maintained substantially conventional architecture.

DESCRIPTION OF THE SPECIFIC EMBODIMENTS

Chimeric hosts are provided comprising functioning xenogeneic hematolymphoid tissue vascularized in the ear pinna of an immunocompromised host. The chimeric host is obtained by isolating tissue from a fetus of a source host. The immunocompromised host is prepared for the tissue by making an incision in the ear pinna. The space formed should readily accommodate the xenogeneic tissue and allow it to be comfortably placed in the space and retained. Once the tissue is introduced, the incision is closed and the host grown. The growth of the tissue may be monitored by visual inspection or by other non-invasive techniques, as appropriate.

The ear pinna as a site for implantation has advantages over previous sites such as the mammary fat pad and kidney capsule. Screening for successful grafts can be easily accomplished by visual inspection of the ear. The pinna is well-vascularized, ensuring a good blood supply to the graft, as well as providing a suitable means for intra-venous (i.v.) injection of infectious agents and/or drugs. Subdermal injection into the pinna also readily reaches the implant. The pinna has other advantages, in its relative lack of solid tissue. Since the ear is mainly skin, connective tissue and blood vessels, the structure of the implant after growth can be determined without the presence of complicating host mammary or kidney tissue.

The chimeric animals may be constructed as a one ear, or two ear model. While one ear will be sufficient for the implant of a single hematolymphoid organ, in some instances it will be desirable to implant tissue in both ears. Implantation into both ears allow study of the movement of elements from one organ to the other. In particular, the mobility of cells or infectious agents such viruses, from one lymphoid organ to another may be determined.

The ease with which an ear is removed allows for kinetic studies of intra-organ mobility. An implanted ear can be removed from the host animal with minimal surgical trauma. Kinetic studies of interest involve the homing of lymphoid and other hematopoietic cells and the maturation of T-cell progenitors.

Suitable lymphoid tissues for implantation are, but are not limited to, fetal lymph node and/or a combined implant of fetal thymus and liver, which grow together to form the hybrid thy-liv organ described in European patent application, publication no. 469 632. The lymph node or thy-liv tissue transplant may be only one of other tissues which are transplanted into the host. The lymph node may serve in the development of a hematopoietic system in the immunocompromised host for a variety of purposes. For example, in addition to the lymph node tissue, other hematopoietic components may be included, such as stem cells, embryonic yolk sac, fetal liver, thymus, spleen, fetal or adult bone marrow tissue, pancreatic tissue, appendix tissue, tonsil tissue and the like. These additional tissues may introduced into the ear site, or at other sites. Sites for introduction may include under the spleen capsule, abdominal wall muscle, under the renal capsule, the peritoneum, the peritoneal lining, brain, subcutaneous, vascular system, spleen, spinal cord, membranous sacs or capsules of various tissue, the retroperitoneal space, reproductive organs, etc.

Desirably, progenitor tissue will be introduced which will be able to mimic, at least in part, a functioning organ. Introduction of the tissue may be achieved by injection, implantation, or joining blood vessels (and other vessels if necessary) of the donor and host, using intravenous catheters, trocars, and/or surgical incision, or the like. The tissue or cells of interest will be normal, non-transformed and non-malignant tissue or cells. With various organs one may include native surrounding tissue with the organ tissue itself. The surrounding tissue may comprise connective tissue, or portions of blood and lymphatic vessels. In some cases, whole organ grafts may be transplanted by anastomosing donor and host blood vessels, lymphatic vessels, and the like. For the most part, normal cells, tissue, and/or organs may be stably maintained and functional for at least three to six months, frequently at least 10 months.

The tissue may be fresh tissue, obtained within about 48 hours of death, or freshly frozen tissue, tissue frozen within about 12 hours of death and maintained at below about −10° C., usually at about liquid nitrogen temperature (−70° C.) indefinitely. The tissue may be from an organ implanted in a chimeric host, where the tissue may be removed from 2–4 weeks after implantation, or longer. In this manner, the tissue originally obtained from the host source may be greatly expanded, substantially increasing the total number of chimeric hosts which may be obtained. The tissue obtained from the chimeric host may be treated analogously to the tissue obtained from the human source. The tissue may be provided as portions of organs or complete organs, comprising or freed from stromal elements, generally from about 0.5 to 4 mm, more usually from about 1 to 2 mm, so that the sections can easily fit into a trocar used for implantation, usually conveniently of about 15- to 20-gauge. Normally the tissue will not have been subject to culture in vitro for an extended period of time.

For the most part the donor cells will be human, although cells from sources other than members of the same family as the host animal may find use. The source of the tissue will usually be fetal. Preferably the tissue will be from a child of less than about 3 years, preferably less than about 1 year and at or younger than neonate, more preferably being fetal tissue of from about 7 to 24 weeks.

For different organs differently aged tissue may be preferred. For fetal tissue, it is desirable that the human lymph node be equal to or greater than about 20 gestational weeks (g.w.), preferably 21–24 g.w.; and for human thymus and liver, from about 16–24 g.w., preferably greater than 18 g.w.

As appropriate, dispersed cells may be employed, where the relevant organs are teased apart to yield viable cells in suspension. Desirably the suspension cells may be enriched for the particular cells of interest. For example, with fetal liver cells, the suspension cells may be enriched for hematopoietic precursors by Ficoll-hypaque density gradient centrifugation. Cells may also be enriched by other techniques, such as fluorescence activated cell sorting, panning, magnetic bead separation, elutriation within a centrifugal field, or rosetting.

In some instances it may be desirable to enrich cells by killing or removing other cells. This may be achieved by employing monoclonal antibodies specific for the undesired cells in the presence of complement or linked to a cytotoxic agent, such as a toxin, e.g. ricin, abrin, diphtheria toxin, or a radiolabel, e.g. $^{131}$I, or the like. Immunoaffinity columns may be employed which allow for specific separation of either the desired or undesired cells, depending on the nature of the mixture.

Immunocompromised mammalian hosts having the desired immune incapacity exist or can be created. The significant factor is that the immunocompromised host is incapable naturally, or in conjunction with the introduced organs, of mounting an immune response against the xenogeneic tissue or cells. Therefore it is not sufficient that a host be immunocompromised, but that the host may not be able to mount an immune response after grafting, as evidenced by the inability to produce competent B-cells, particularly plasma cells, and/or T-cells, particularly $CD4^+$ and/or $CD8^+$ T-cells. Of particular interest are hosts, e.g. mice, which are immunocompromised in lacking functional syngeneic B and T lymphocytes as a result of a genetic defect in immunoglobulin and T-cell receptor gene rearrangement. Hosts which are presently available include hosts which have severe combined immunodeficiency, known as scid/scid, or the Rag-1$^-$ and/or Rag-2$^-$ hosts, which lack recombinase competence due to introduction of a genetic defect at the indicated loci.

The host will usually be of an age less than about 25% of the normal lifetime of an immunocompetent host, usually about 1 to 20% of the normal lifetime. Generally, the host will be at least about six weeks old and large enough to manipulate for introduction of the donor mammalian cells at the desired site. For example, mice are usually used at about 6 to 10 weeks of age. Growth of the tissue within the host will vary with the organ.

The mammalian host will be grown in conventional ways. Depending on the degree of immunocompromised status of the mammalian host, it may be protected to varying degrees from infection. In some instances a sterile environment or prophylactic antibiosis may be indicated. Prophylactic antibiosis may be achieved for SCID mice with 25–75 mg trimethoprim and 100–300 mg sulfamethoxazole in 5 ml of suspension, given three days each week. Alternatively, it may be satisfactory to isolate the potential xenogeneic hosts from other animals in germ-free environments after cesarean derivation. The feeding and maintenance of the chimeric host will for the most part follow conventional techniques.

The presence of the foreign tissue in an immunocompromised host may be used to study the effect of various compounds on the growth, viability, differentiation, maturation, transformation, or the like, of the foreign cells in a live host. The chimeric host may be used to study the effect of a variation of a condition on a symptom or indication of a disease. By condition, it is intended a physical, chemical or biological property, e.g. temperature, electric potential, ionic strength, drugs, transformation, etc.

It is of particular interest to study the pathogenesis of various infectious agents and/or the effect of various drugs or treatments on the induction or progress of disease. Infectious agents of interest include bacteria, such as Pneumococcus, Staphylococcus, Streptococcus, Meningococcus, Gonococcus, Eschericia, Klebsiella, Proteus, Pseudomonas, Salmonella, Shigella, Hemophilus, Yersinia, Listeria, Corynebacterium, Vibrio, Clostridia, Chlamydia, Mycobacterium, Helicobacter and Treponema; protozoan pathogens, and viruses. Viruses of interest include HIV; enteric viruses, e.g. coxsackie, echovirus, reovirus; respiratory viruses, e.g. rhinovirus, adenovirus, coronavirus, parainfluenzavirus, influenzavirus; picornavirus; rhabdovirus; rubcola; poxvirus; herpesvirus; EBV; paramyxovirus and cytomegalovirus.

Exemplary of such a pathogenic model is infection with HIV. Infection may be achieved by direct injection. Usually, the injection will involve at least about $10^2$ infectious units, preferably from about $10^3$ to $10^5$ infectious units of HIV. The HIV may be a clinical isolate, a cloned clinical isolate, a genetically modified isolate, or the like. The HIV should not have been cultured in tissue culture for an extended period.

Various drugs may be administered to the host and the effect on a particular tissue determined by invasive or non-invasive techniques. Non-invasive techniques include NMR, CAT scans, fluoroscopy, roentgenography, radionuclide scanning, ultrasonography, electrocardiography, electroencephalography, evoked potentials, etc. Invasive techniques include biopsy, autopsy, laparotomy, laparoscopy, intermittent intravenous blood sampling, or intravenous catheterization, etc. Convenient placement of various devices, e.g. catheters, electrodes, etc. may be performed for continuous monitoring. Thus, the host be used to determine the carcinogenicity of various compounds to different xenogeneic tissues, the effect on growth and viability of various xenogeneic tissues, the effect of combinations of compounds, e.g. drugs, or the like. In addition, by providing for pathogenic infection of the xenogeneic tissue, the effect of various drugs in protecting the host tissue from the pathogen, as well as being cytotoxic to or suppressive of the pathogen in a cellular environment can be determined.

The chimeric host may also be used for evaluating the cytotoxicity of various drugs toward the foreign tissue, for example, for screening for investigative new drug applications. In addition, the chimeric hosts may be used for evaluating drugs as to their efficacy, safety and bio-availability. Use of the chimeric animal in studying the effect of drugs on infection may begin with administration of the drug prior to, substantially concomitant with, or subsequent to the administration of the infectious dose of virus. Administration of the drug will usually begin not earlier than 7 days prior to infection, more usually not more than about 1 day prior to infection. In most cases, administration of the drug will begin not later than about 7 days after infection, more usually not later than about 1 day after infection. However, for studies of chronic infections, drug treatment may be started after as much as one year after infection, usually after six months, more usually after one month. After initial screening, different periods of time may be of interest in establishing the effectiveness of the drug.

The manner of administration will vary greatly, depending upon the nature of the drug. It may be provided orally, ad libitum, intraperitoneally, intravascularly, subcutaneously, intrathymically, or the like. Usually, different dosage levels will be employed, based on past experience with the drug, anticipated levels with human treatment, toxicity or side effects, experience with the particular chimeric host, and the like. The effect of the drug may be monitored for any convenient time, usually at least 1 week from the initiation of administration of the drug, more usually at least 2 weeks, and at times for periods as long as 6 weeks or more. Preferably, determinations will be made in the period from about 2–6 weeks.

For the effectiveness of drugs in suppressing HIV-induced T-cell or thymocyte depletion, various measurements can be made. By employing flow cytometry (fluorescence-activated cell scanning flow cytometry), one can analyze the CD4 and CD8 profile of the peripheral blood, the cell population in a cell dispersion prepared from the lymph node implant, or other human fetal tissue which is present, as appropriate. One may also monitor for the presence of HIV, by monitoring the level of p24 in the peripheral blood or the implant, HIV RNA or portion thereof, or HIV DNA, using the polymerase chain reaction. In addition, one may use histological analysis, employing immunochemistry, for detecting the presence of CD4, CD8 and p24 or other proteins of HIV, which are present in the implant. One may also analyze for indications of apoptosis in the infected tissue, as indicated by multiple foci of cells with condensed nuclear material as seen by histologic methods or election microscopy or as determined by methods which can discern a DNA degradation profile consistent with apoptosis.

Phenotyping of the xenogeneic cells to verify their origin and stage developmental progression may be performed by standard histological methods, by immunohistochemistry, antibody staining or in situ hybridization with RNA and/or DNA probes. The exact method is not critical to the invention, and will depend on the exact cell types being studied.

HLA markers may be used to distinguish the established xenogeneic organ transplants from the cells. The HLA type can be readily determined by staining with an appropriate antibody directed against any of the alleles of the human HLA locus, including Class I and Class II antigens.

The following examples are offered by way of illustration and not by way of limitation.

EXPERIMENTAL

Example 1

Implantation of Fetal Lymph Node into Ear Pinna

Whole human fetal mesenteric lymph nodes of 20–24 gestational weeks in age were dissected out from the donor. The surrounding mesenteric vessels were generally cut away, although they were not observed to affect the implant if left attached to the lymph node. The tissue was obtained directly in the operating room as fetal parts. Without maintaining strict sterility the parts were taken immediately to a gross dissection room. The identified tissue was dissected out and placed into RPMI 1640 medium with 10% fetal calf serum.

CB.17 scid/scid mice were anesthetized with ketamine and a 1 mm slice was cut off to expose the tip of the ear. Forceps were used to gently pull apart the sides of the ear, to form a pocket 2–3 mm deep. Holding the outer flap of the ear pinna with forceps, another pair of forceps is gently inserted, and advanced by slowly opening and closing the forceps, forming a deeper pocket that runs between blood vessels. This pocket reached to almost the base of the pinna. A dissected lymph node is gently inserted into the pocket, and the ear sealed with a light dab of cyanoacrylate glue.

The mice were maintained on a normal diet using trimethoprim/sulfamethoxazole (40 mg/200 mg per 5 ml of suspension; 0.125 ml of suspension per 4 ml of drinking water per mouse per day).

Histology slides from chimeric animals 3, 5 and 7 weeks after implantation were examined. The 3 week and 7 week implants had good cellularity with a small amount of necrosis. In all cases the ear pinna had a healthy appearance and the lymphoid tissue was vascularized.

Cells were taken from implanted lymph nodes 2–6 weeks after implantation, and stained with antibodies against the CD4 and CD8 antigens, or against CD19 and CD45 antigens. For the most part CD4 and CD8 are expressed by helper or killer T-cells, respectively. CD19 is expressed by B cells, and CD45 is expressed by all hematopoietic cells except erythrocytes. The control lymph nodes and thymus were taken from fetuses of 20–22 gestational weeks. The staining results are presented in Table 1.

TABLE 1

| | | | | Transplanted Lymph Nodes | | | | | | | |
| | | | | % Positive Cells | | | | | | | |
| No. | Donor | Age | Wks post | CD45 | CD4 | CD8 | CD19 | CD25 | Class II | CD4/ CD8 | T-Cells |
| --- | --- | --- | --- | --- | --- | --- | --- | --- | --- | --- | --- |
| 9268.1 | SF297 | 24 | 6 | 87.5 | 48.1 | 22.7 | 0.0 | | | 2.1 | 70.8 |
| 9268.2 | SF297 | 24 | 6 | 79.0 | 28.6 | 22.7 | 1.5 | | | 1.3 | 51.3 |
| 9268.3 | SF297 | 24 | 6 | 43.1 | 25.8 | 3.4 | 4.3 | | | 7.6 | 29.2 |
| 9268.4 | SF297 | 24 | 6 | 56.9 | 27.7 | 13.4 | 2.8 | | | 2.1 | 41.1 |
| 9268.5 | SF297 | 24 | 6 | 54.4 | 28.1 | 17.6 | 1.4 | | | 1.6 | 45.6 |
| 9346.1 | K1123 | 22 | 4 | 85.2 | 26.6 | 28.4 | 0.3 | | | 0.9 | 55.0 |
| 9346.2 | K1123 | 22 | 4 | 83.9 | 67.1 | 8.1 | 0.5 | | | 8.3 | 75.2 |
| 9413.1 | K1127 | 24 | 4 | 92.7 | 75.1 | 7.2 | 0.6 | 23.4 | 30.3 | 10.5 | 82.3 |

TABLE 1-continued

| | | | | | | | | | Class | CD4/ | T |
|---|---|---|---|---|---|---|---|---|---|---|---|
| | | | | CD45 | CD4 | CD8 | CD19 | CD25 | II | CD8 | cells |
| 9413.3 | K1127 | 24 | 4 | 87.5 | 65.1 | 13.2 | 0.8 | 9.1 | 25.4 | 4.9 | 78.3 |
| 9474.1 | K1131 | 21.5 | 4 | 71.8 | 50.0 | 8.2 | 4.0 | 5.0 | 40.1 | 6.1 | 58.2 |
| 9474.3 | K1131 | 21.5 | 4 | 86.9 | 18.1 | 40.8 | 1.3 | 5.1 | 58.8 | 0.4 | 58.9 |
| 9714.1 | K1146 | 20 | 2 | 57.6 | 24.7 | 33.3 | 5.6 | 16.1 | | 0.7 | 58.1 |
| 9714.2 | K1146 | 20 | 2 | 63.4 | 49.4 | 26.3 | 2.2 | 28.4 | | 1.9 | 75.6 |
| 9714.3 | K1146 | 20 | 2 | 65.4 | 38.8 | 30.9 | 2.3 | 21.5 | | 1.3 | 69.7 |
| 9714.4 | K1146 | 20 | 2 | 71.6 | 45.0 | 24.2 | 3.2 | 35.9 | | 1.9 | 70.0 |
| 9714.5 | K1146 | 20 | 2 | 67.9 | 43.9 | 25.1 | 2.5 | 28.2 | | 1.7 | 69.0 |
| 9687.1 | L498 | 20 | 2 | 52.7 | 48.8 | 21.4 | 2.7 | 17.9 | | 2.3 | 70.0 |
| 9687.2 | L498 | 20 | 2 | 78.1 | 68.7 | 17.1 | 4.1 | 33.5 | | 4.0 | 85.7 |
| 9687.3 | L498 | 20 | 2 | 69.3 | 59.4 | 24.4 | 2.9 | 27.4 | | 2.4 | 83.8 |
| 9687.4 | L498 | 20 | 2 | 64.8 | 51.9 | 28.1 | 2.7 | 29.5 | | 1.9 | 80.0 |
| 9687.5 | L498 | 20 | 2 | 67.9 | 52.2 | 30.0 | 2.4 | 30.0 | | 1.7 | 82.3 |
| 9836.1 | L504 | 21 | 2 | 82.8 | 64.6 | 14.4 | 1.4 | 31.2 | | 4.5 | 79.0 |
| 9836.2 | L504 | 21 | 2 | 78.0 | 52.8 | 15.9 | 2.8 | 29.0 | | 3.3 | 68.6 |
| 9836.3 | L504 | 21 | 2 | 84.4 | 70.5 | 9.3 | 0.7 | 42.8 | | 7.6 | 79.8 |
| 9836.4 | L504 | 21 | 2 | 85.6 | 69.4 | 11.4 | 0.9 | 46.3 | | 6.1 | 80.9 |

Summary of Implanted Lymph Nodes

| | CD45 | CD4 | CD8 | CD19 | CD25 | Class II | CD4/CD8 | T cells |
|---|---|---|---|---|---|---|---|---|
| Mean: | 72.7 | 48.0 | 19.9 | 2.1 | 18.4 | 6.2 | 3.5 | 67.9 |
| SD: | 13.2 | 17.0 | 9.5 | 1.4 | 11.6 | 14.8 | 2.7 | 14.8 |

Summary of Control Unimplanted Lymph Nodes

| | CD45 | CD4 | CD8 | CD19 | CD25 | Class II | CD4/CD8 | T cells |
|---|---|---|---|---|---|---|---|---|
| Mean: | | 58.0 | 27.2 | 4.5 | 7.7 | 10.2 | 2.3 | 85.1 |
| SD: | | 6.9 | 5.5 | 1.8 | 2.9 | 1.4 | 1.1 | 2.2 |

The staining data shows that the implanted lymph nodes are able to maintain their cellularity. Both the number of T cells, and the proportion of CD4 to CD8 T-cells was well maintained in comparison with the control, non-implanted lymph nodes.

Example 2

Infection of Lymph Node Implants with HIV

In a laminar flow hood, HIV, at a titer of $4 \times 10^3$ IU/ml, was loaded into a syringe with 30 G needle. The needle was inserted sub-dermally toward the lymph node, without hitting the node. When the needle bevel reached under the skin surface, the virus solution was slowly injected. Injection was stopped when the lymph node became enclosed with virus solution.

CB.17 scid/scid mice implanted with a human fetal lymph node were infected with HIV 2 weeks after implantation. Two weeks after infection, the implanted lymph node was removed, and assayed for the presence of HIV. Assays for virus were performed by several methods, by measuring the amount of viral p24 protein, or by detecting viral nucleic acid sequences. The lymph node tissue had high levels of viral p24, from 560 to 3108 picograms/ml.

PCR was used to detect either viral DNA and/or RNA. The RNA assay used guanidium isothiocyanate extraction of RNA, followed by cDNA synthesis, then PCR amplification of the cDNA. Positive controls using primers specific for human β-globin DNA were done at the same time as amplification for HIV sequences.

TABLE 2

HIV INFECTION OF IMPLANTED LYMPH NODES

| | | Transplant | | | | Virus | | Term. | | PCR | |
|---|---|---|---|---|---|---|---|---|---|---|---|
| Cage | M# | Date | Donor | Age | Infect. Date | Strain | Route | Day | §-glob | DNA | RNA |
| 9558 | .1 | 6-9-93 | K1137 | | 6-24-93 | EW | iv/sd | 14 | + | + | − |
| 9558 | .2 | 6-9-93 | K1137 | | 6-24-93 | EW | iv/sd | 14 | + | + | − |
| 9558 | .3 | 6-9-93 | K1137 | | 6-24-93 | EW | iv/sd | 14 | + | + | − |
| 9558 | .4 | 6-9-93 | K1137 | | 6-24-93 | EW | iv | 14 | + | − | − |
| 9558 | .5 | 6-9-93 | K1137 | | | (−) | | 14 | + | − | − |
| 9559 | .1 | 6-9-93 | K1137 | | 6-24-93 | EW | iv | 14 | + | − | − |
| 9559 | .2 | 6-9-93 | K1137 | | 6-24-93 | EW | iv | 14 | + | − | − |
| 9559 | .3 | 6-9-93 | K1137 | | 6-24-93 | EW | sd | 14 | + | + | − |
| 9559 | .4 | 6-9-93 | K1137 | | 6-24-93 | EW | sd | 14 | + | + | − |
| 9559 | .5 | 6-9-93 | K1137 | | 6-24-93 | EW | sd | 14 | + | + | − |
| 9591 | .1 | 6-17-93 | SF321 | 20 | 6-30-93 | XHO | iv | 14 | + | − | − |
| 9591 | .2 | 6-17-93 | SF321 | 20 | 6-30-93 | XHO | iv | 14 | + | − | − |
| 9591 | .3 | 6-17-93 | SF321 | 20 | 6-30-93 | XHO | iv | 14 | + | − | − |
| 9591 | .4 | 6-17-93 | SF321 | 20 | 6-30-93 | XHO | iv/sd | 14 | + | + | − |
| 9591 | .5 | 6-17-93 | SF321 | 20 | 6-30-93 | XHO | iv/sd | 14 | + | + | − |
| 9591 | .1 | 6-17-93 | SF321 | 20 | 6-30-93 | XHO | iv/sd | 14 | + | + | − |
| 9590 | .2 | 6-17-93 | SF321 | 20 | 6-30-93 | XHO | sd | 14 | + | + | − |

TABLE 2-continued

| | | Transplant | | | | Virus | | Term. | | PCR | |
|---|---|---|---|---|---|---|---|---|---|---|---|
| Cage | M# | Date | Donor | Age | Infect. Date | Strain | Route | Day | §-glob | DNA | RNA |
| 9590 | .3 | 6-17-93 | SF321 | 20 | 6-30-93 | XHO | sd | 14 | + | + | − |
| 9590 | .4 | 6-17-93 | SF321 | 20 | 6-30-93 | XHO | sd | 14 | + | + | − |
| 9590 | .5 | 6-17-93 | SF321 | 20 | | (−) | | 14 | + | − | − |

The results with injection of several HIV isolates, Xho-3 D3 and EW WS-1 D2 show that sub-dermal (s.d.) injection of virus into the ear pinna was an effective route for infection of the implanted lymph node with HIV. The presence of HIV DNA was demonstrated by the positive result in the PCR assay. Intravenous injection (i.v.) was not effective, as the animals infected by i.v. alone were not positive for HIV DNA.

The change in distribution of T cell subsets was also monitored after virus injection. Cells were taken from implanted lymph nodes, and implanted-injected lymph nodes, and stained with antibodies against CD4 and CD8. When the injected virus was the molecular clone NL-4, there was no depletion of the CD4+ subset after injection. However, injection of a clinical isolate, EW D-2, gave an inversion of the CD4/CD8 ratio after injection. The number of B cells remained normal.

A summary of the change in cellularity and T cell subset distribution is shown in Table 3. It can be seen that there is an inversion in the ratio of CD4/CD8 positive cells, and a decrease in the percent of cells which are T cells after injection of HIV.

TABLE 3

Time Course of Change in T cell Distribution

| | DAYS AFTER INJECTION | | | | | | |
|---|---|---|---|---|---|---|---|
| | Day 4 | Day 7 | Day 10 | Day 14 | Day 21 | control | transplant control |
| % CD4+ | 68.2 | 53.9 | 35.8 | 17.1 | 7.3 | 58 | 44.9 |
| % CD8+ | 7.4 | 18 | 27.8 | 41.6 | 36 | 27.2 | 21.3 |
| CD4/CD8 | 9.5 | 4.4 | 1.8 | .5 | .5 | 2.3 | 3.1 |
| % T cells | 75.6 | 73 | 62.3 | 58.5 | 46.6 | 85.1 | 67.9 |

It is evident from the above results, that a valuable animal model is provided for the growth of human fetal lymphoid tissue. The tissue can be infected with HIV, and the effect of various HIV isolates on T cell subsets can be determined.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A mouse host which is immunocompromised in lacking functional syngeneic B and T lymphocytes as a result of a genetic defect in immunoglobulin and T-cell receptor gene rearrangement, comprising vascularized viable xenogeneic non-malignant, non-transformed human fetal lymph node tissue in at least one ear pinna.

2. A host according to claim 1, wherein said mouse host is a scid/scid mouse.

3. A host according to claim 1, wherein said lymph node tissue is capable of being infected with a virus.

4. A host according to claim 3, wherein said virus is HIV.

5. A mouse host which is immunocompromised in lacking functional syngeneic B and T lymphocytes as a result of a genetic defect in immunoglobulin and T-cell receptor gene rearrangement, comprising HIV infected, viable xenogeneic non-malignant, non-transformed human fetal lymph node tissue in at least one ear pinna.

6. A mouse host according to claim 5, wherein said host is a C.B17 scid/scid mouse.

7. A method for producing a chimeric mammal comprising a xenogeneic lymph node engrafted into an ear pinna, said method comprising:

inserting through an incision human fetal lymph node tissue into the ear pinna of a mouse host which is immunocompromised in lacking functional syngeneic B and T lymphocytes as a result of a genetic defect in immunoglobulin and T-cell receptor gene rearrangement; and closing said incision and maintaining said mouse whereby said tissue becomes vascularized.

8. A method according to claim 7, wherein said mouse host is a scid/scid mouse.

9. A method according to claim 8, wherein said vascularized tissue is capable of being infected with a virus.

10. A method according to claim 9, wherein said virus is HIV.

* * * * *